(12) United States Patent
Hobro et al.

(10) Patent No.: US 11,065,374 B2
(45) Date of Patent: Jul. 20, 2021

(54) RENAL FAILURE THERAPY SYSTEM AND METHOD OF CLEANING USING CITRIC ACID

(71) Applicant: GAMBRO LUNDIA AB, Lund (SE)

(72) Inventors: Sture Hobro, Lund (SE); Jonas Fors, Malmoe (SE); Olof Jansson, Vellinge (SE)

(73) Assignee: GAMBRO LUNDIA AB, Lund (SE)

( * ) Notice: Subject to any disclaimer, the term of this patent is extended or adjusted under 35 U.S.C. 154(b) by 0 days.

(21) Appl. No.: 16/326,095

(22) PCT Filed: Aug. 16, 2017

(86) PCT No.: PCT/EP2017/070749
§ 371 (c)(1),
(2) Date: Feb. 15, 2019

(87) PCT Pub. No.: WO2018/033566
PCT Pub. Date: Feb. 22, 2018

(65) Prior Publication Data
US 2019/0201606 A1 Jul. 4, 2019

(30) Foreign Application Priority Data

Aug. 18, 2016 (SE) .................................... 1651113-1

(51) Int. Cl.
*A61M 1/16* (2006.01)
*A61M 1/36* (2006.01)

(52) U.S. Cl.
CPC ........ *A61M 1/1688* (2014.02); *A61M 1/1605* (2014.02); *A61M 1/168* (2013.01);
(Continued)

(58) Field of Classification Search
CPC .... A61M 1/169; A61M 1/1686; A61M 1/168; A61M 1/1688; A61M 1/1656;
(Continued)

(56) References Cited

U.S. PATENT DOCUMENTS 5,173,125 A 12/1992 Felding
5,304,349 A 4/1994 Polaschegg
(Continued)

FOREIGN PATENT DOCUMENTS

WO 2015/071244 A1 5/2015

OTHER PUBLICATIONS

International Search Report and Written Opinion for related International Application No. PCT/EP2017/070749, dated Oct. 26, 2017; (16 pages).
(Continued)

*Primary Examiner* — Claire A Norris
(74) *Attorney, Agent, or Firm* — K&L Gates LLP

(57) ABSTRACT

A renal failure therapy system (10a, 10b) includes a dialysis fluid circuit (30) including a dialysis fluid pump (54, 58); a source (86, 90) of physiological cleaning, disinfecting, and/or decalcifying substance in fluid communication with the dialysis fluid circuit; a source (22) of purified water in fluid communication with the dialysis fluid circuit; and a logic implementer (20) in operable communication with the dialysis fluid pump (54,58), the logic implementer (20) causing the physiological cleaning, disinfecting, and/or decalcifying substance from its source (86, 90) to be added to purified water from the purified water source (22) to form a mixture and to circulate the mixture within the dialysis fluid circuit using the dialysis fluid pump (54,58) to at least one of clean, disinfect or decalcify at least a portion of the dialysis fluid circuit (30) without a subsequent rinse.

17 Claims, 6 Drawing Sheets

(52) U.S. Cl.
CPC ........... *A61M 1/1694* (2013.01); *A61M 1/169* (2013.01); *A61M 1/3643* (2013.01); *A61M 2205/3331* (2013.01)

(58) Field of Classification Search
CPC ...... A61M 1/14; A61M 1/3649; A61M 1/166; A61M 1/1664; C02F 2303/04
USPC ................................... 210/636, 646, 321.71
See application file for complete search history.

(56) References Cited

U.S. PATENT DOCUMENTS

| | | | |
|---|---|---|---|
| 5,853,014 | A | 12/1998 | Rosenauer |
| 8,529,487 | B2 | 9/2013 | Fava et al. |
| 9,956,308 | B2 | 5/2018 | Schreyer et al. |
| 10,092,686 | B2 | 10/2018 | Hobro et al. |
| 10,780,186 | B2 | 9/2020 | Felding et al. |
| 2002/0179518 | A1 | 12/2002 | Ho |
| 2013/0020237 | A1* | 1/2013 | Wilt .................... A61M 1/1654 210/85 |
| 2014/0190887 | A1 | 7/2014 | Rohde et al. |
| 2014/0217020 | A1 | 8/2014 | Meyer et al. |

OTHER PUBLICATIONS

Chinese Office Action from corresponding Chinese Patent Application No. 201780064628.X, dated Mar. 16, 2021.

\* cited by examiner

RENAL FAILURE THERAPY SYSTEM AND METHOD OF CLEANING USING CITRIC ACID

PRIORITY CLAIM

The present application is a National Phase of International Application No. PCT/EP2017/070749, filed Aug. 16, 2017, which claims priority to Swedish Application No. 1651113-1, filed Aug. 18, 2016, the entire contents of each of which are incorporated herein by reference and relied upon.

BACKGROUND

The present disclosure relates generally to medical systems and methods. More specifically, the present disclosure relates to renal failure therapy systems and methods of cleaning same.

Hemodialysis ("HD") in general uses diffusion to remove waste products from a patient's blood. A diffusive gradient that occurs across the semi-permeable dialyzer between the blood and an electrolyte dialysis solution causes diffusion. Hemofiltration ("HF") is an alternative renal replacement therapy that relies on a convective transport of toxins from the patient's blood. This therapy is accomplished by adding substitution or replacement fluid to the extracorporeal circuit during treatment (typically ten to ninety liters of such fluid). The substitution fluid and the fluid accumulated by the patient in between treatments is ultrafiltered over the course of the HF treatment, providing a convective transport mechanism, which is particularly beneficial in removing middle and large molecules (in hemodialysis there is a small amount of waste removed along with the fluid gained between dialysis sessions, however, the solute drag from the removal of that ultrafiltrate is typically not enough to provide convective clearance).

Hemodiafiltration ("HDF") is a treatment modality that combines convective and diffusive clearances. HDF flows dialysis fluid through a dialyzer, similar to standard hemodialysis, providing diffusive clearance. In addition, substitution solution is provided directly to the extracorporeal circuit, providing convective clearance.

The above modalities are provided by a dialysis machine. The machines may be provided in a center or in a patient's home. Dialysis machines provided in a center are used multiple times a day for multiple patients and are therefore cleaned between treatments. There are different processes for cleaning dialysis machines that use different cleaning agents. One type of cleaning agent is citric acid. Known steps of the citric acid cleaning process include a rinsing phase in which the citric acid cleaning agent is flushed from the machine. The flushing step may vary between fifteen and twenty minutes.

For in center dialysis in particular, time is money. While the dialysis machine is down in between treatments, a patient cannot be dialyzed. Also, downtime generally means nurse time. When dialysis treatment is running smoothly, the nurse does not have to attend the machine constantly and may be off performing other tasks. Nursing time is expensive too. There is accordingly a need to reduce downtime between hemodialysis treatments as much as possible.

SUMMARY

The present disclosure provides a renal failure therapy system and method that performs hemodialysis ("HD"), hemofiltration ("HF"), hemodiafiltration ("HDF"), peritoneal dialysis ("PD"), isolated ultrafiltration ("UF"), slow continuous ultrafiltration ("SCUF"), continuous renal replacement therapy ("CRRT"), continuous veno-venous hemodialysis ("CVVHD"), continuous veno-venous hemofiltration ("CVVH"), and continuous veno-venous hemodiafiltration ("CVVHDF"). Accordingly, "renal failure therapy" as used herein is meant to include any one, or more, or all of the above modalities.

The present disclosure takes advantage of the fact that citric acid used to disinfect a dialysis machine between treatments is a weak human organic acid. It is in fact a natural preservative/conservative and is used to add an acidic or sour taste to foods and drinks. In biochemistry, citric acid is important as an intermediate in the citric acid cycle, which occurs in the metabolism of higher organisms. Citric acid and citrate are related compounds. That is, at a physiologically safe pH, citric acid exists predominantly in an ionized form, which is known as citrate. It is an example of a chemical equilibrium reached in a biological system. When citric acid meets blood, including the blood's bicarbonate content, the citric acid transforms into to citrate.

In dialysis, citrate (a salt of citric acid, may be in combination with citric acid itself) is used, inter alia, as an anticoagulant. For example, assuming a blood flow of 300 ml/minute, a concentration of about 3.5 mmol citrate may be introduced into the patient's extracorporeal circuit at a flowrate of about 0.2 gram/minute. Calcium is added when using citrate to ensure a minimal concentration of free calcium in the patient's bloodstream. The patient accordingly tolerates 6 to 12 grams of citrate per hour using citrate anticoagulant.

Knowing that the patient may tolerate small levels of citric acid, the system and method of the present disclosure seek to streamline the disinfection process between dialysis treatments, e.g., in a center, using citric acid as the disinfectant, by removing the complete flushing phase. Much of the citric acid may be drained from the system during a partial drain (e.g., ten percent to seventy-five percent (10% to 75%) of total dialysis fluid circuit volume) at the end of the disinfection sequence. Another portion of the citric acid is flushed from the machine flow path during the startup of the machine for a new treatment. The startup of the machine from a citric acid cleaning may take 3 to 4 minutes. Further, it has become more and more common to prime the line set for the next treatment using dialysis fluid, wherein, for example, bicarbonate and A-concentrate are regulated to a proper or desired level (normally 4 to 8 minutes), during which the citric acid will be further flushed from the system.

In one example sequence, at the end of treatment, the used dialysis fluid in the dialysis machine is drained completely. The disinfection sequence of the present disclosure is then commenced. First, the dialysis fluid side of the machine is filled with purified water, such as reverse osmosis ("RO") water. The dialysis fluid pumps are used to perform the filling. During the water filling step, citric acid is added to the water as a disinfectant. The blood side of the machine in one embodiment constitutes a disposable set, which is discarded between treatments, and is thus not part of the disinfection sequence.

The citric acid has multiple effects, one, along with hot water cleaning, is to clean the dialysis fluid circuit from precipitates of calcium carbonate (i.e., limestone), which is often called decalcification. Second, citric acid also reinforces heat disinfection, and indeed improves the heat disinfection using water only during a prescribed time and for a given temperature. For example, it has been published that adding two to three percent (2% to 3%) citric acid achieves heat disinfection obtained from disinfection using pure water but heated to ten degrees higher. Varying heat and citric acid levels allows the user to desirably balance disinfection effectiveness, disinfection time, and machine wear.

One suitable citric acid dry concentrate container, marketed as CleanCart®, provides 32 grams of citric acid to the water filling the dialysis fluid circuit. The dialysis fluid circuit in one embodiment holds about two to three liters of water. The water and citric acid filling step may take, for example, one to two minutes.

In a second disinfection step, the water and citric acid mixture is heated, e.g., to a higher temperature of 60-93° C. The heater used is in one embodiment the dialysis fluid heater provided with the dialysis machine. The heating step may last approximately one to thirty minutes depending on the heating temperature and the amount of disinfection needed. During the heating step, the water and citric acid are circulated past the heater to help heat the fluid uniformly and completely. The circulation also helps to blend the water and citric acid.

In a third disinfection step, the heated water and citric acid solution or mixture is circulated around the dialysis fluid circuit using the dialysis fluid pumps. The heated mixture may be pumped back and forth to create a washing motion and to ensure that all inner workings of the tubing and dialysis fluid components are contacted. This third cleaning step may vary between one and thirty minutes. The dialysis machine may or may not flush some of the water and citric acid without replacing the cleaning fluid, so that some of the citric acid is removed from the dialysis fluid circuit and is exchanged with new and heated purified, e.g., RO water. It is estimated that the exchanges remove about thirty to seventy percent of the original concentration of citric acid.

In a fourth disinfection step, the dialysis machine performs a partial or full drain. One example of a full drain is when the machine attempts to drain itself as much as possible, which may lead to a drain of about eighty to ninety-five percent (80% to 95%) of all fluid within the dialysis fluid circuit. An example partial drain may then be when it is not intended for the machine to drain completely and instead drain only partially, e.g., from about ten to seventy-five percent (10% to 75%) empty. The full and partial drains also serve to remove heat from the dialysis fluid circuit (assuming heat has been added via the disinfection fluid). The dialysis fluid for the next patient needs to be at body temperature, e.g., about 37° C.

A partial drain will accordingly remove about 10% to 75% of the citric acid in the flow path. However when water and dialysis fluid is later introduced into the machine, the new fluid will pressurize one or more air cushion with the fluid remaining in the machine from the partial drain. The one or more air cushion will cause the difference in the removal of citric acid between a full drain and a partial drain to be minimal.

Thus, by the end of the partial drain (when the air front reaches the end of the flow path, only about three (3) grams of citric acid should remain in the dialysis fluid circuit (assuming 32 grams of citric acid is added initially). The remaining citric acid level is accordingly already below the six (6) to twelve (12) grams of citrate that the patient may tolerate using citrate anticoagulant. The limited drain may last one or two minutes.

In a fifth step, the filling or priming of the dialysis machine for the next patient removes much of the, e.g., three (3) grams of citric acid remaining after the limited drain. During the filling or priming for the next patient, which may last five to ten minutes, acid and bicarbonate are added to the purified, e.g., RO, water to make dialysis solution, which is physiologically compatible with the patient's blood. The filling or priming step also includes exchanges to push air to drain and thereby removes about ninety percent (90%) of the three (3) grams of citric acid left after the limited drain. Thus, only about, e.g., 0.3 gram of the original 32 grams of citric acid from the disinfection sequence remains after filling or priming.

Charts are provided below illustrating that the effect of citric acid on pH while forming dialysis fluid is overcome in a matter of minutes. For both bicarbonate and acetate type of dialysis fluid preparation, a "green fluid path" (meaning it is OK to proceed with therapy) is reached within minutes.

Of the 0.3 gram of citric acid remaining after filling or priming, it may be assumed that only half of it, e.g., about 0.15 to 0.2 gram, resides on the upstream or fresh dialysis fluid side of the dialysis fluid circuit. That is, the other part of the 0.3 gram of citric acid is presumed to reside on the downstream or used fluid side of the dialysis fluid circuit. Dialysis fluid residing on the used fluid side of the dialysis fluid circuit cannot reach the patient and will instead be flushed to drain. Moreover, of the, e.g., 0.15 to 0.2 gram of citric acid residing on the fresh fluid side of the dialysis fluid circuit, only a portion will reach the patient. Some of the, e.g., 0.15 to 0.2 gram may be ultrafiltered into substitution fluid which is delivered directly to the blood circuit. Some of the, e.g., 0.15 to 0.2 gram of citric acid may osmose across the dialyzer membranes into the blood circuit. Some of the, e.g., 0.15 to 0.2 gram of citric acid however will flow through the dialysis fluid compartment, into the used fluid side of the dialysis fluid circuit, to drain. In the end, a very small, negligible amount of citric acid is delivered to the patient.

Various alternatives to the above-described sequence are contemplated. For example, it may be possible to shorten or even eliminate the cleaning or limited drain steps. It may also be possible to raise the initial concentration of citric acid, e.g., to 50 grams or so, and use a shorter, third cleaning step, so that the overall cleaning level remains approximately the same.

In light of the technical features set forth herein, and without limitation, in a first aspect, a renal failure therapy system includes: a dialysis fluid circuit including a dialysis fluid pump; a source of physiological cleaning, disinfecting, and/or decalcifying substance in fluid communication with the dialysis fluid circuit; a source of purified water in fluid communication with the dialysis fluid circuit; and a logic implementer in operable communication with the dialysis fluid pump, the logic implementer programmed to cause the physiological cleaning, disinfecting, and/or decalcifying substance to be added from its source to purified water from the purified water source to form a mixture and to circulate the mixture within the dialysis fluid circuit using the dialysis fluid pump to at least one of clean, disinfect or decalcify at least a portion of the dialysis fluid circuit without a subsequent rinse.

In a second aspect, which may be used with any other aspect described herein unless specified otherwise, the physiological cleaning, disinfecting, and/or decalcifying substance includes an acid.

In a third aspect, which may be used with the second aspect in combination with any other aspect described herein unless specified otherwise, the acid is at least partially citric acid.

In a fourth aspect, which may be used with any other aspect described herein unless specified otherwise, the physiological cleaning, disinfecting, and/or decalcifying substance includes citric acid in combination with a physiologically safe substance.

In a fifth aspect, which may be used with any other aspect described herein unless specified otherwise, a filling procedure for a subsequent treatment is used to remove a portion of the mixture to drain.

In a sixth aspect, which may be used with the fifth aspect in combination with any other aspect described herein unless specified otherwise, the filling procedure involves the introduction of a bicarbonate substance from a source that neutralizes the physiological cleaning, disinfecting, and/or decalcifying substance.

In a seventh aspect, which may be used with the fifth aspect in combination with any other aspect described herein unless specified otherwise, the filling procedure removes at least one percent of an original amount of the physiological cleaning, disinfecting, and/or decalcifying substance.

In an eighth aspect, which may be used with the fifth aspect in combination with any other aspect described herein unless specified otherwise, the renal failure therapy system includes a heater, the logic implementer programmed to control the heater during the filling procedure to heat a filling fluid to a temperature below 35° C. to cool the dialysis fluid circuit.

In a ninth aspect, which may be used with the eighth aspect and any other aspect described herein unless specified otherwise, the logic implementer further programmed to cause the heater to heat the mixture while at least one of cleaning, disinfecting or decalcifying the at least a portion of the dialysis fluid circuit.

In a tenth aspect, which may be used with any other aspect described herein unless specified otherwise, the logic implementer in a drain sequence programmed to remove a portion of the mixture to drain.

In an eleventh aspect, which may be used with the tenth aspect in combination with any other aspect described herein unless specified otherwise, the drain sequence is a partial drain sequence.

In a twelfth aspect, which may be used with any other aspect described herein unless specified otherwise, wherein the logic implementer is programmed to cause the physiological cleaning, disinfecting, and/or decalcifying substance to be added from its source to purified water from the purified water source to form the mixture and to circulate the mixture within the dialysis fluid circuit using the dialysis fluid pump to at least one of clean, disinfect or decalcify at least a portion of the dialysis fluid circuit without a subsequent rinse or a subsequent drain.

In a thirteenth aspect, which may be used with the fifth aspect in combination with any other aspect described herein unless specified otherwise, the renal failure therapy system includes a source of concentrate in fluid communication with the dialysis fluid circuit, and wherein the logic implementer is programmed to cause concentrate from the concentrate source to be mixed with the remaining mixture during the filling procedure to form dialysis fluid for the subsequent treatment.

In a fourteenth aspect, which may be used with any other aspect described herein unless specified otherwise, the renal failure therapy system includes a blood set, wherein the blood set is removed while the dialysis fluid pump at least one of cleans, disinfects or decalcifies the at least a portion of the dialysis fluid circuit without a subsequent rinse.

In a fifteenth aspect, which may be used with the fifth aspect and any other aspect described herein unless specified otherwise, a renal failure therapy machine is operable with a source of physiological cleaning, disinfecting, and/or decalcifying substance and a source of purified water, the machine including: a dialysis fluid circuit including a dialysis fluid pump, the dialysis fluid circuit configured to pump from the physiological cleaning, disinfecting, and/or decalcifying substance source and the purified water source; and a logic implementer in operable communication with the dialysis fluid pump, the logic implementer programmed to cause: (i) the physiological cleaning, disinfecting, and/or decalcifying substance from its source to be added to purified water from the purified water source to form a mixture and to circulate the mixture within the dialysis fluid circuit using the dialysis fluid pump to at least one of clean, disinfect or decalcify at least a portion of the dialysis fluid circuit after a first treatment, (ii) a portion of the mixture to be drained in a drain sequence, and (iii) a filling procedure for a second treatment to begin with the mixture remaining in the dialysis fluid circuit, the filling procedure relied upon to reduce the mixture remaining to a lower level.

In a sixteenth aspect, which may be used with the fifteenth aspect in combination with any other aspect described herein unless specified otherwise, the logic implementer is programmed to circulate the mixture within the dialysis fluid circuit from about one (1) to about thirty (30) minutes.

In a seventeenth aspect, which may be used with the fifteenth aspect in combination with any other aspect described herein unless specified otherwise, wherein during (iii) at least one percent of an original amount of the physiological cleaning, disinfecting, and/or decalcifying substance is removed.

In an eighteenth aspect, which may be used with the fifteenth aspect in combination with any other aspect described herein unless specified otherwise, wherein during (iii) a bicarbonate substance from a source is provided, which neutralizes the physiological cleaning, disinfecting, and/or decalcifying substance.

In a nineteenth aspect, which may be used with any other aspect described herein unless specified otherwise, a cleaning method for a renal failure therapy machine includes: pumping purified water and a physiological cleaning, disinfecting, and/or decalcifying substance to form a mixture; pumping the mixture to at least one of clean, disinfect or decalcify at least a portion of a dialysis fluid circuit; draining a portion of the mixture from the dialysis fluid circuit; and moving to a subsequent treatment without performing a rinse.

In a twentieth aspect, which may be used with the nineteenth aspect in combination with any other aspect described herein unless specified otherwise, wherein the drained portion of the mixture is a first portion, and wherein moving to the subsequent treatment includes performing a filling procedure that drains a second portion of the mixture.

In a twenty-first aspect, which may be used with the nineteenth aspect in combination with any other aspect described herein unless specified otherwise, wherein draining a portion of the mixture from the dialysis fluid circuit includes trapping air in the dialysis fluid circuit.

In a twenty-second aspect, which may be used with any other aspect described herein unless specified otherwise, the system includes at least one of (i) a keyed connector for the source of physiological cleaning, disinfecting, and/or decalcifying substance and a mating keyed connector for the dialysis fluid circuit, or (ii) a marking associated with the source of physiological cleaning, disinfecting, and/or decalcifying substance and a scanner, reader, RFID reader, or camera in communication with logic implementer for reading the marking, upon which logic implementer may allow or confirm the circulating of the mixture without the subsequent rinse.

In a twenty-third aspect, which may be used with any other aspect described herein unless specified otherwise, the dialysis fluid circuit includes a disinfection recirculation loop and an air separation chamber located within the loop, the air separation chamber increasing at least one of flowrate and heating efficiency of the physiological cleaning, disinfecting, and/or decalcifying substance flowing within the disinfection recirculation loop.

In a twenty-fourth aspect, any of the features, functionality and alternatives described in connection with any one or more of FIG. 1A to 7 may be combined with any of the features, functionality and alternatives described in connection with any of the other one or more of FIG. 1A to 7.

In light of the above aspects and the teachings herein, it is therefore an advantage of the present disclosure to provide a hemodialysis, hemofiltration or hemodiafiltration system and method that reduces machine downtime.

It is another advantage of the present disclosure to provide a hemodialysis, hemofiltration or hemodiafiltration system and method that reduces nurse interaction.

It is a further advantage of the present disclosure to provide a hemodialysis, hemofiltration or hemodiafiltration system and method that reduces treatment cost.

Moreover, it is an advantage of the present disclosure to provide a hemodialysis, hemofiltration or hemodiafiltration system and method that uses an environmentally safe disinfecting agent.

The advantages discussed herein may be found in one, or some, and perhaps not all of the embodiments disclosed herein. Additional features and advantages of the present invention are described in, and will be apparent from, the following Detailed Description of the Invention and the figures.

DETAILED DESCRIPTION

Figure 1A:
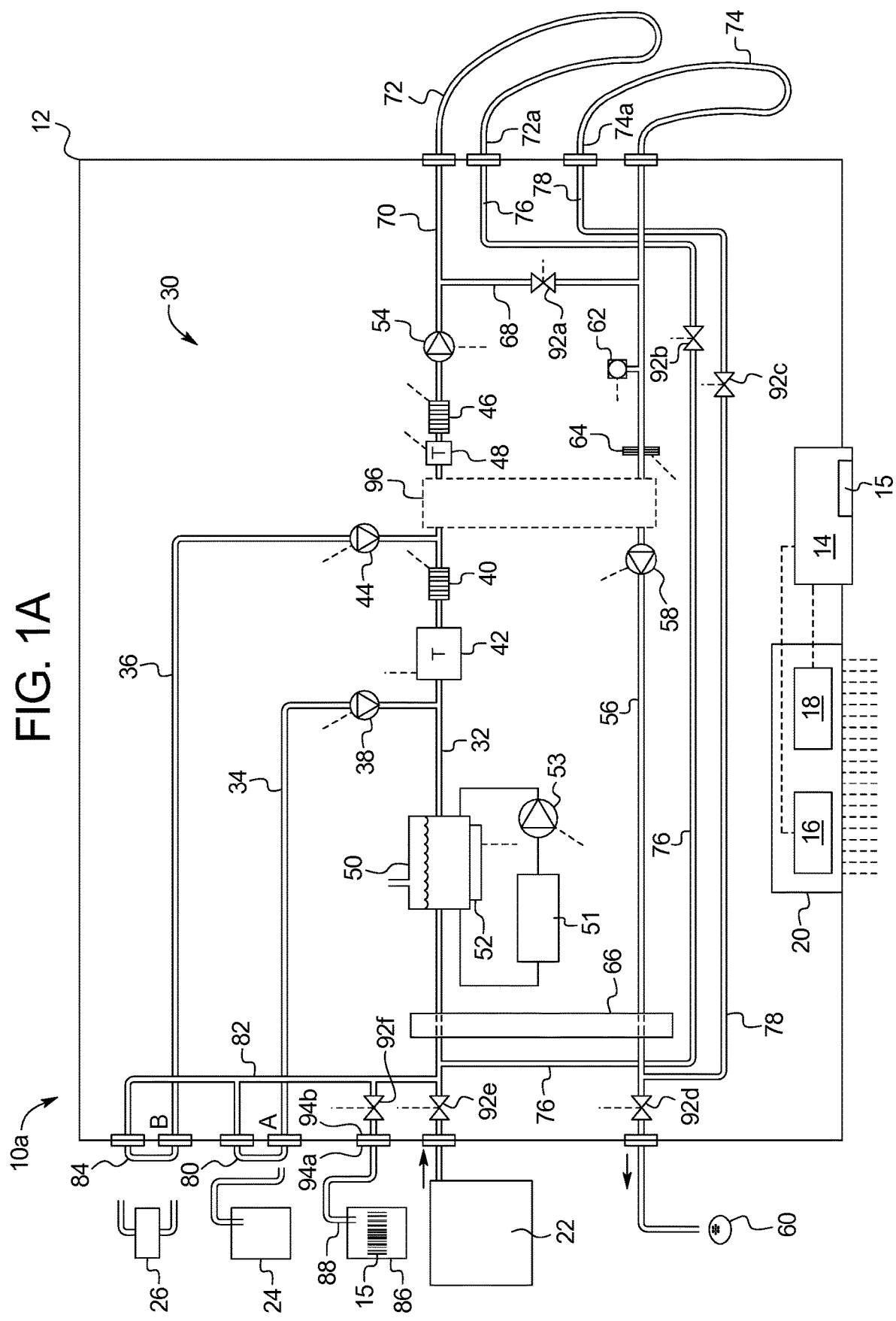
FIG. 1A is a schematic illustration of one embodiment of a renal therapy system including a citric acid liquid source, which may be used with the disinfection sequence or method of the present disclosure.
Figure 1B:
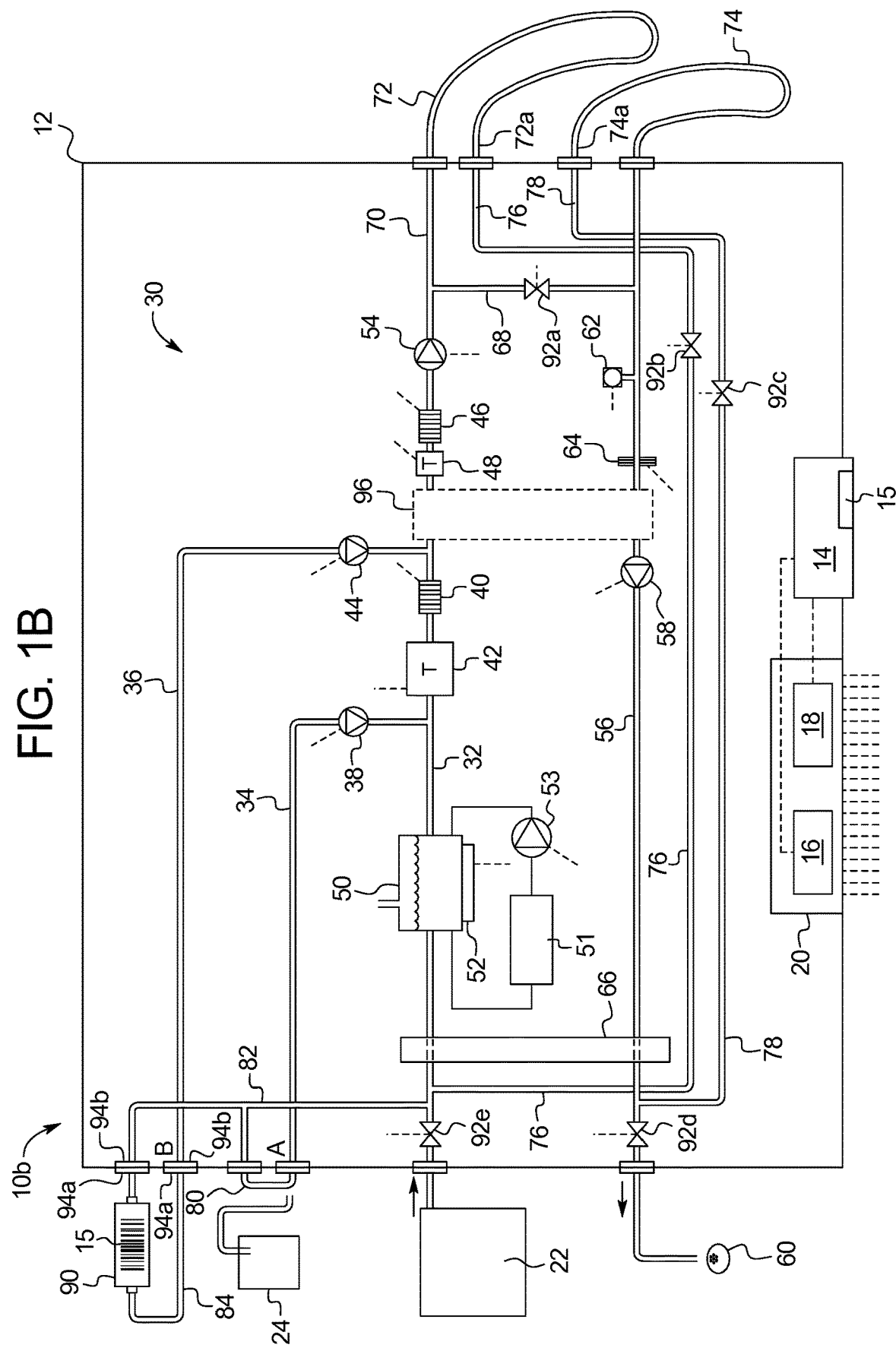
FIG. 1B is a schematic illustration of one embodiment of a renal failure therapy system including a dry powder citric acid cartridge, which may be used with the disinfection sequence or method of the present disclosure.

Referring now to the drawings and in particular to FIGS. 1A and 1B, embodiments of the system of the present disclosure are illustrated by systems 10a and 10b. Systems 10a and 10b each include a machine 12 having a housing. Machine 12 holds the contents of a dialysis fluid circuit 30 described in detail below. Machine 12 also supports a user interface 14, which allows a nurse or other operator to interact with systems 10a and 10b. User interface 14 may have a monitor screen operable with a touch screen overlay, electromechanical buttons, e.g., membrane switches, or a combination of both. User interface 14 is in electrical communication with at least one processor 16 and at least one memory 18. At least one processor 16 and at least one memory 18 also electronically interact with, and where appropriate, control the pumps, valves and sensors described herein, e.g., those of dialysis fluid circuit 30. At least one processor 16 and at least one memory 18 are referred to collectively herein as a logic implementer 20. The dashed lines extending from logic implementer 20 lead to pumps, valves, sensors, the heater and other electrical equipment, as indicated by like dashed lines leading from the pumps, valves, sensors, heater, etc.

Dialysis fluid circuit 30 includes a purified water line 32, an A-concentrate line 34 and a bicarbonate B-concentrate line 36. Purified water line 32 receives purified water from a purified water device or source 22. The water may be purified using any one or more process, such as, reverse osmosis, carbon filtering, ultraviolet radiation, electrodeionization ("EDI"), and/or ultrafiltering. One suitable device or source 22 for purifying the water is marketed as a WRO 300 H™ water purification machine.

An A-concentrate pump 38, such as a peristaltic or piston pump, pumps A-concentrate from an A-concentrate source 24 into purified water line 32 via A-concentrate line 34. Conductivity cell 40 measures the conductive effect of the A-concentrate on the purified water, sends a signal to logic implementer 20, which uses the signal to properly proportion the A-concentrate by controlling A-concentrate pump 38. The A-conductivity signal is temperature compensated via a reading from temperature sensor 42.

A B-concentrate pump 44, such as a peristaltic or piston pump, pumps B-concentrate, e.g., a bicarbonate substance, from a B-concentrate source 26 into purified water line 32 via B-concentrate line 36. Conductivity cell 46 measures the conductive effect of the B-concentrate on the purified water/A-concentrate mixture, sends a signal to logic implementer 20, which uses the signal to properly proportion the B-concentrate by controlling B-concentrate pump 44. The B-conductivity signal is also temperature compensated via a reading from temperature sensor 48.

An expansion tank 50 deaerates the purified water prior to receiving the concentrates, removing bubbles from the water, which has been degassed in a chamber 51 via a degassing pump 53, located below expansion tank 50. A heater 52 controlled by logic implementer 20 heats the purified water for treatment to body temperature, e.g., 37° C. The fluid exiting conductivity cell 46 is therefore freshly prepared dialysis fluid, properly degassed and heated, and suitable for sending to a dialyzer for treatment. A fresh dialysis fluid pump 54, such as a gear pump, delivers the fresh dialysis fluid to a dialyzer (see FIG. 3). Logic implementer 20 controls fresh dialysis fluid pump 54 to deliver fresh dialysis fluid to the dialyzer at a specified flowrate.

A used dialysis fluid pump 58 located along drain line 56 pumps used dialysis fluid from the dialyzer to a drain 60.

Logic implementer 20 controls used dialysis fluid pump 58 to pull used dialysis fluid from the dialyzer at a specified flowrate. A pressure sensor 62 senses the pressure of spent dialysis fluid within drain line 56 and sends a corresponding pressure signal to logic implementer 20. A blood leak detector 64, such as an optical detector, looks for the presence of blood in drain line, e.g., to detect if a dialyzer membrane has a tear or leak. A heat exchanger 66 recoups heat from the used dialysis fluid exiting dialysis fluid circuit 30 to drain 60, preheating the purified water traveling towards heater 52 to conserve energy.

UF system 96 monitors the flowrate of fresh dialysis fluid flowing to dialyzer 102 (and/or as substitution fluid flowing directly to the blood set (FIG. 3)) and used fluid flowing from the dialyzer. UF system 96 includes fresh and used flow sensors as part of a UF System Control, which sends signals to logic implementer 20 indicative of the fresh and used dialysis fluid flowrate, respectively. Logic implementer 20 uses the signals to set used dialysis fluid pump 58 to pump faster than fresh dialysis fluid pump 54 by a predetermined amount to remove a prescribed amount of ultrafiltration ("UF") from the patient over the course of treatment. A second set of fresh and used flow sensors may be provided as part of UF System Protective, which are redundant sensors that ensure UF system 96 is functioning properly.

A bypass line 68 allows fresh dialysis fluid to flow from fresh dialysis fluid line 70 to drain line 56 without contacting the dialyzer. A fresh dialysis fluid tube 72 extends from the housing of machine 12 and carries fresh dialysis fluid from fresh dialysis fluid line 70 to the dialyzer. A used dialysis fluid tube 74 also extends from the housing of machine 12 and carries used dialysis fluid from the dialyzer to drain line 56.

During disinfection, the distal end 72a of fresh dialysis fluid tube 72 is not connected to the dialyzer and is instead plugged into machine 12, so as to sealingly communicate with a fresh disinfection recirculation line 76, which feeds into purified water line 32 upstream of heat exchanger 66. Disinfection fluid may therefore be circulated through purified water line 32, fresh dialysis fluid line 70, fresh dialysis fluid tube 72 and fresh disinfection recirculation line 76.

Likewise, during disinfection the distal end 74a of used dialysis fluid tube 74 is not connected to the dialyzer and is instead plugged into machine 12, so as to sealingly communicate with used disinfection recirculation line 78, which feeds drain line 56 downstream of used dialysis fluid pump 58. Disinfection fluid may therefore be circulated through drain line 56, used dialysis fluid tube 74 and used disinfection recirculation line 78.

Also during disinfection, A-concentrate supply 24 and B-concentrate supply 26 are disconnected from dialysis fluid circuit 30 as illustrated in FIGS. 1A and 1B and plugged into machine 12. A shunt line 80 is placed instead at the A-concentrate connection to machine 12, fluidly connecting the A-concentrate line 34 to a water supply branch line 82. Disinfection fluid may therefore be circulated through A-concentrate line 34, shunt line 80 and water supply branch line 82.

The differences between system 10a of FIG. 1A and system 10b of FIG. 1B are that in system 10a of FIG. 1A, a second shunt line 84 is placed at the B-concentrate connection to machine 12, fluidly connecting the B-concentrate line 36 to water supply branch line 82. Disinfection fluid may therefore be circulated through B-concentrate line 36, second shunt line 84 and water supply branch line 82. Also in FIG. 1A, citric acid concentrate in liquid form is provided from a source 86 via a citric acid supply line 88 to water supply branch line 82. A- or B-concentrate pump 38 or 44 under control of logic implementer 20 may meter a desired amount of liquid citric acid concentrate from supply 86 into the fresh recirculation loop, including fresh disinfection recirculation line 76, using water supply branch line 82. Bypass line 68 may be opened to allow the citric acid disinfectant to reach used recirculation loop including used disinfection recirculation line 78. Thus, the entire dialysis fluid circuit 30 may be disinfected. Heat from heater 52 is also used for disinfection in one embodiment.

Although not illustrated, systems 10a and 10b may place an air trap type structure at the junction between used disinfection recirculation line 78 and drain line 56, just to the right of drain valve 92d. The air trap type structure separates air from whatever liquid is flowing through drain line 56, so that the air may be pushed to drain 60, leaving degassed liquid to flow back through used disinfection recirculation line 78.

In system 10b of FIG. 1B, liquid citric acid concentrate source 86 and citric acid supply line 88 are not used. Instead, a flow-through dry concentrate source or cartridge 90, such as the CleanCart® cartridge, is inserted into second shunt line 84 and is thus placed in fluid communication with water supply branch line 82 and B-concentrate line 36. B-concentrate pump 44 pulls purified water through water supply branch line 82, dry concentrate source or cartridge 90, second shunt line 84, and B-concentrate line 36 into the fresh recirculation loop including fresh disinfection recirculation line 76 and the used recirculation loop including used disinfection recirculation line 78 via opened bypass line 68. Thus, the entire dialysis fluid circuit 30 in system 10b may be disinfected. Heat from heater 52 is also used for disinfection in system 10b.

In system 10b, the dry concentrate is provided in an amount appropriate for the volume of dialysis fluid circuit 30, including shunt line 84 and dialysis fluid tubes 72 and 74, assuming that all of the powder from source 90 is dissolved fully into the purified water. In an embodiment, fully dissolving all the powder from the CleanCart® cartridge introduces 32 grams of citric acid into dialysis fluid circuit 30. The CleanCart® cartridge contains citric acid anhydrate powder, and is used in one embodiment in combination with heat disinfection to both decalcify and disinfect the dialysis fluid circuit simultaneously. The resulting citric acid solution while circulated removes precipitates of calcium and magnesium carbonates.

Systems 10a and 10b of FIGS. 1A and 1B each provide plural valves 92 (collectively referring to valves 92a to 92f) under the control of logic implementer 20 to selectively control a filling or priming procedure before treatment, the dialysis treatment, disinfection after treatment, and other sequences and procedures involved with systems 10a and 10b. In particular, valve 92a selectively opens and closes bypass line 68, e.g., to allow disinfection fluid to flow from the fresh dialysis fluid circulation loop to the used dialysis fluid circulation loop. Valve 92b selectively opens and closes fresh disinfection recirculation line 76. Valve 92c selectively opens and closes used disinfection recirculation line 78. Valve 92d selectively opens and closes drain line 56 to drain 60, which is an important pathway for the citric acid disinfection sequence described in more detail below. Valve 92e selectively opens and closes purified water line 32 to purified water source 22, which is also an important pathway for the citric acid disinfection sequence described in more detail below. Valve 92*f* for system 10*a* (not system 10*b*) selectively opens and closes water supply branch line 82 to citric acid source 86.

It should be appreciated that the dialysis fluid circuits 30 of FIGS. 1A and 1B are simplified and may include other structure and functionality not illustrated. Also, dialysis fluid circuits 30 of FIGS. 1A and 1B illustrate a hemodialysis ("HD") pathway. It is expressly contemplated to provide one or more ultrafilter in fresh dialysis fluid line 70 to create substitution fluid for hemofiltration ("HF"). It is also expressly contemplated to provide one or more ultrafilter in one or more line(s) branching off of fresh dialysis fluid line 70 to create substitution fluid, in addition to the fresh dialysis fluid in line 70, for hemodiafiltration ("HDF"). In each case, the disinfection sequences described below would also reach and disinfect any additional or alternative tubing, filters, pumps, valves and other associated structure.

Figure 2:
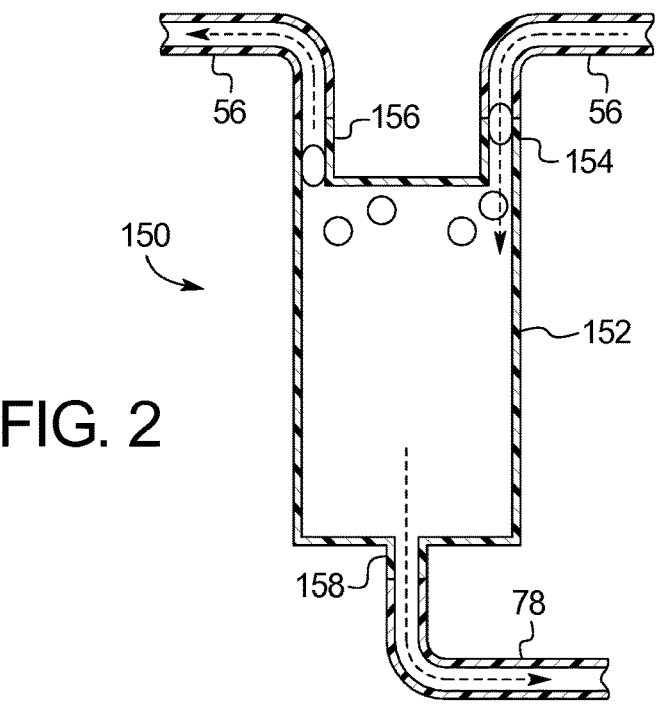
FIG. 2 is an elevation view of one embodiment for an air separation device placed at the end of a drain line as part of a disinfection recirculation loop.

Referring now to FIG. 2, in an alternative embodiment, either one or both of systems 10*a* and 10*b* of FIGS. 1A and 1B may replace (or add adjacent to) its drain valve 92*d* with an air separation chamber 150. Air separation chamber 150 is made of a suitable medical grade plastic or metal in various embodiments. Air separation chamber 150 includes a chamber housing 152, a liquid/air inlet 154, a liquid/air outlet 156, and a pure (or almost pure) liquid outlet 158. The liquid at various times may be used dialysis fluid, purified water, or heated water with a physiologically safe cleaning agent as described herein, such as citric acid. As used herein, a physiologically safe substance may be one that in its current or in a diluted form is safe for injection into a patient's bloodstream.

Liquid/air inlet 154 and liquid/air outlet 156 as illustrated in FIG. 2 splice into drain line 56 of systems 10*a* and 10*b* of FIGS. 1A and 1B. Liquid outlet 158 as illustrated in FIG. 2 connects to used disinfection recirculation line 78 of systems 10*a* and 10*b* of FIGS. 1A and 1B. In effect, air separation chamber 150 replaces the tee in FIGS. 1A and 1B, where used disinfection recirculation line 78 meets with drain line 56 line just upstream of drain valve 92*d*. Again, air separation chamber 150 may or may not take the place of drain valve 92*d*.

Air separation chamber 150 removes air from used dialysis fluid circulation loop, which includes drain line 56 and used disinfection recirculation line 78. The air is removed primarily via buoyancy forces as illustrated in FIG. 2. Air separation chamber 150 may employ baffles or other structures within chamber housing 152 if desired to help separate air from whatever type of liquid is present. The removal of air helps to fill the disinfection recirculation loop 56, 78 with less air and consequently more fluid to improve flowrate, which in turn helps the efficiency of cleaning, disinfecting and decalcifying.

The volume of chamber housing 152 of air separation chamber 150 helps to fill lines 56 and 78 of the recirculation loop 56, 78 because water fills chamber housing 152 instead of flowing to drain 60, trapping heat, and thereby allowing the temperature of the cleaning, disinfecting and decalcifying fluid to rise more quickly. Also, as the liquid level within chamber housing 152 rises, air is released from the fluid to drain, such that the cleaning, disinfecting and decalcifying fluid tends to become dearated during the filling of disinfection recirculation loop 56, 78. Again, improved heating efficiency and dearated cleaning, disinfecting and decalcifying fluid help to improve the overall efficiency of the cleaning, disinfecting and decalcifying. Moreover, electromechanical drain valve 92*d* may be removed from systems 10*a* and 10*b*, decreasing cost and overall component wear.

In an embodiment, a liquid level sensor (not illustrated), such as an ultrasonic, capacitive, inductive sensor or optical sensor, is positioned adjacent chamber housing 152 of air separation chamber 150, such that the sensor may sense when chamber housing 152 is full or almost full. The liquid level sensor is in logic communication with logic implementer 20 and changes output level or state when the liquid level transitions from not full to full (or almost full) and vice versa. Logic implementer 20 uses the level sensor signal to toggle bypass valve 92*a* to (i) open to fill chamber housing 152 until the level sensor reads full (or almost full) and (ii) close when chamber housing 152 is full (or almost full) until the liquid level falls below the liquid level sensor, changing its output again to reopen bypass valve 92*a*. In this manner, disinfection fluid does not flow out of chamber housing 152 and is therefore not wasted to drain 60.

Figure 3:
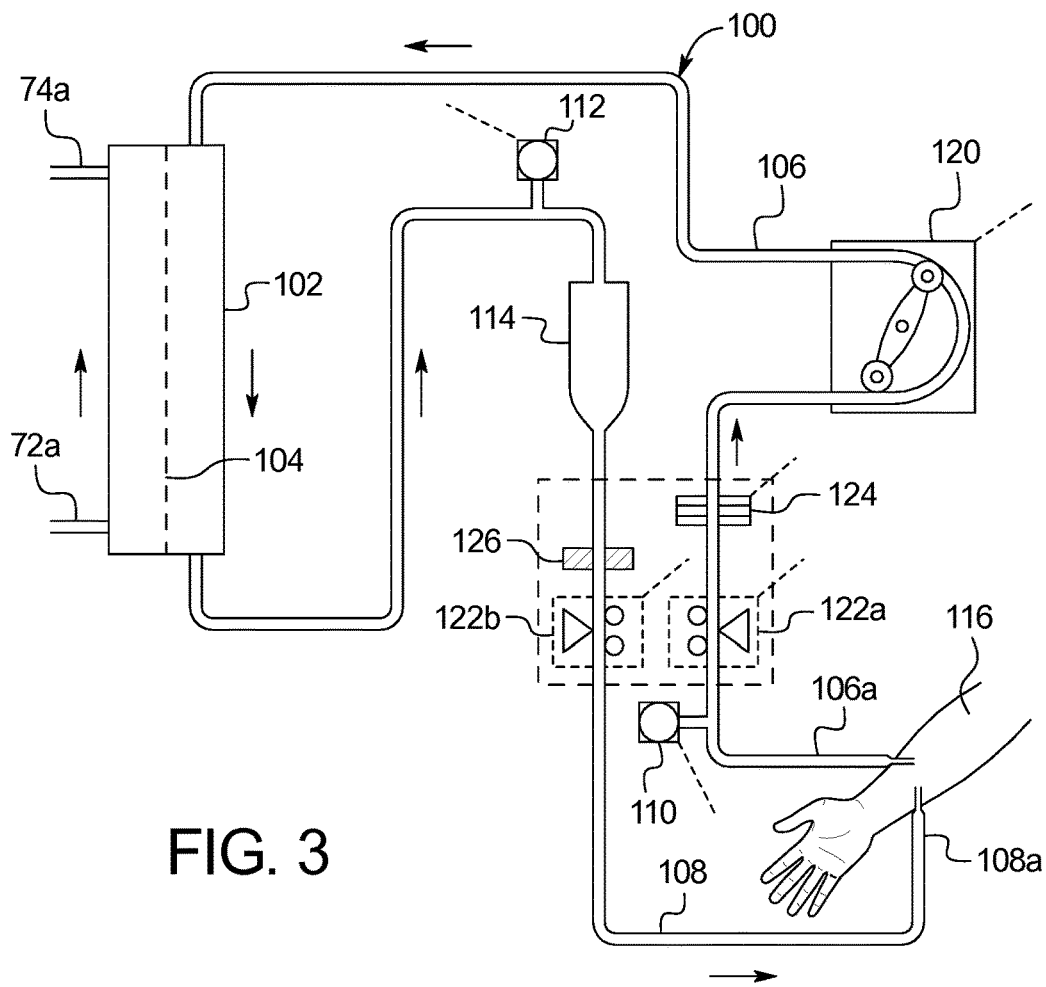
FIG. 3 is an elevation cross-sectional view of one embodiment of a hemodialysis blood set, which may be used with the disinfection sequence or method of the present disclosure

Referring now to FIG. 3, blood set 100 illustrates one embodiment of a blood set that may be used with either system 10*a* or 10*b*. Blood set 100 includes a dialyzer 102 having many hollow fiber semi-permeable membranes 104, which separate dialyzer 102 into a blood compartment and a dialysis fluid compartment. The dialysis fluid compartment during treatment is placed in fluid communication with distal end 72*a* of fresh dialysis fluid tube 72 and distal end 74*a* of used dialysis fluid tube 74. FIGS. 1A and 1B illustrate that during disinfection and priming, distal ends 72*a* and 74*a* are instead plugged sealingly into disinfection recirculation lines 76 and 78, respectively. It should be appreciated that for HF, replacement fluid flows from a substitution line (not illustrated) directly to one or both arterial line 106 and venous line 108 of blood set 100, while fresh dialysis fluid line 70 is occluded so that fresh dialysis fluid does not flow to dialyzer 102. For HDF, replacement fluid flows from the substitution line (not illustrated) directly to one or both arterial line 106 and venous line 108 of blood set 100, while fresh dialysis fluid line 70 is opened so that fresh dialysis fluid flows additionally to dialyzer 102.

Arterial pressure pod 110, located upstream of blood pump 120, enables arterial line pressure to be measured, while venous line 108 includes a venous pressure pod 112, enabling venous line pressure to be measured. Pressure pods 110 and 112 operate with blood pressure sensors (not seen) mounted on the housing of machine 12, which send arterial and venous pressure signals, respectively, to logic implementer 20. Venous line 108 includes a venous drip chamber 114, which removes air from the patient's blood before the blood is returned to patient 116.

Arterial line 106 of blood set 100 includes a portion operable with blood pump 120, which is under the control of logic implementer 20 to pump blood at a desired flowrate. Systems 10*a* and 10*b* also provide multiple blood side electronic devices that send signals to and/or receive commands from logic implementer 20. For example, logic implementer 20 commands pinch clamps 122*a* and 122*b* to selectively open or close arterial line 106 and venous line 108, respectively. A blood volume sensor ("BVS") 124 is located along arterial line 106 upstream of blood pump 120. Air detector 126 looks for air in venous blood line 108. Air detector 126 looks for air in venous blood line 108.

Figure 4:
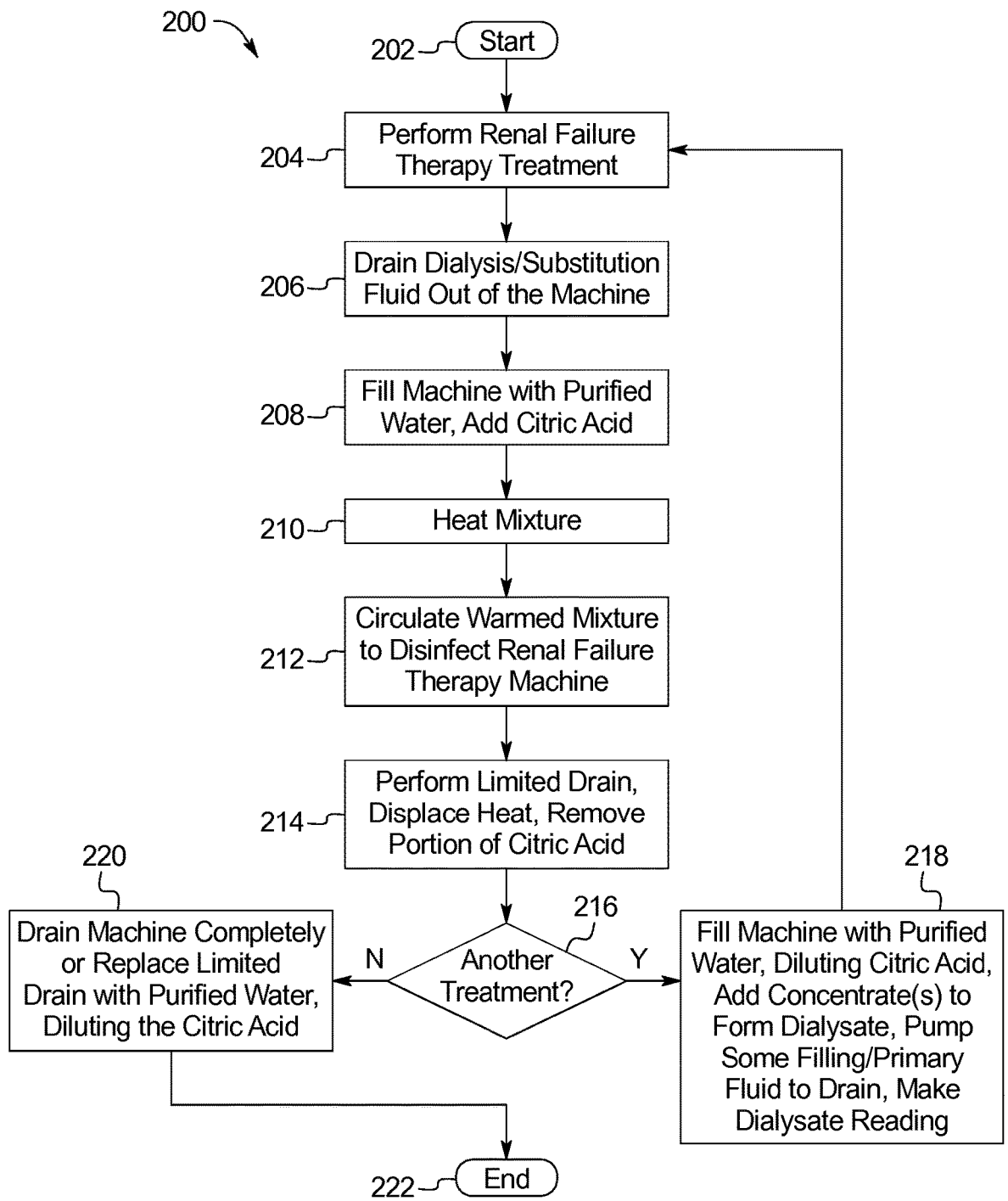
FIG. 4 is a process flow diagram illustrating one embodiment of a disinfection sequence of the present disclosure, which may be automated using the example systems of FIGS. 1A and 1B.

Referring now to FIG. 4, one embodiment of a sequence or method of the present disclosure is illustrated by method 200. Method 200 may be stored on one or more memory device 18 of logic implementer 20. One or more processor 16 of logic implementer 20 runs method 200 automatically in one embodiment at the end of treatment. At step 202, method 200 begins. At step 204, system 10*a* or 10*b* performs a renal failure therapy treatment, such as hemodialysis ("HD"), hemofiltration ("HF") or hemodiafiltration ("HDF"). The dialysis fluid is a physiological fluid that will act as a nutrition solution for many types of bacteria. Bacteria may enter dialysis fluid circuit 30 and together with the dialysis fluid begin to multiply. Also, dialysis fluid is not a stable solution and over time some precipitation will occur within dialysis fluid circuit 30. Accordingly, the dialysis fluid circuit 30 and in particular drain line 56 (due to the risk of cross-contamination from patient to patient) needs to be disinfected regularly to ensure that no excessive bacterial growth starts in the machines of systems 10a or 10b. At the end of step 204, blood set 100 and dialyzer 102 may be removed from system 10a or 10b as has been discussed herein.

At step 206, logic implementer 20 causes fresh dialysis fluid pump 54 and used dialysis fluid pump 58 to send all residual fresh and used dialysis fluid and/or substitution fluid and blood filtrated fluid within dialysis fluid circuit 30 to drain via drain line 56. If pure hemodialysis is performed, dialysis fluid pumps 54 and 58 pump residual fresh and used dialysis fluid to drain. If pure hemofiltration is performed, pumps 54 and 58 pump residual fresh substitution fluid and blood filtrated fluid to drain. If hemodiafiltration is performed, pumps 54 and 58 pump residual fresh and used dialysis fluid and fresh substitution fluid and blood filtrated fluid to drain. In any case, dialysis fluid circuit 30 may be essentially dry after step 206 or be partially drained as discussed above.

At step 208, logic implementer 20 adds citric acid to purified water in dialysis circuit 30. As discussed above, purified water source 22 may purify the water using any one or more process, such as, reverse osmosis, carbon filtering, ultraviolet radiation, electrodeionization ("EDI"), and/or ultrafiltering. In one embodiment, citric acid is blended first in the fresh recirculation loop where valve 92a is closed, valves 92b and 92e are opened, allowing citric acid and water to blend in fresh dialysis fluid line 70 and fresh disinfection recirculation line 76. The blended citric acid/water is then introduced into the used recirculation loop including drain line 56 and used disinfection recirculation line 78 by opening valve 92a.

For example, in system 10a of FIG. 1A, concentrate pump 38 or 44 may pull liquid citric acid concentrate from source 86, through branch water line 82, a shunt line 80 or 84, and A-concentrate line 34 or B-concentrate line 36, into purified water line 32, while fresh dialysis fluid pump 54, with bypass valve 92a closed, circulates the mixture within fresh dialysis fluid line 70 and fresh disinfection recirculation line 76. Then, the blended citric acid/water is introduced into the used recirculation loop including drain line 56 and used disinfection recirculation line 78 by opening valve 92a.

In another example using system 10b of FIG. 1B, B-concentrate pump 44 may pull purified water through branch water line 82 and dry powder citric acid cartridge 90, through B-concentrate line 36, into purified water line 32/dialysis fluid line 70, while fresh dialysis fluid pump 54, with bypass valve 92a closed, circulates the mixture within fresh dialysis fluid line 70 and fresh disinfection recirculation line 76. Then, the blended citric acid/water is introduced into the used recirculation loop including drain line 56 and used disinfection recirculation line 78 by opening valve 92a. Again, one suitable dry powder citric acid cartridge 90 is marketed under the trade name CleanCart®.

When valve 92a is opened to allow the blended citric acid and purified water into used recirculation loop, including drain line 56 and used disinfection recirculation line 78, additional water is pulled from purified water source 22 to fill the additional volume of the used recirculation loop. The additional purified water dilutes the citric acid concentration.

Following the example of system 10b, dialysis fluid pumps 54 and 58 circulate the purified water through dry concentrate cartridge 90 until all or most all of the citric acid concentrate powder dissolved into the purified water. The CleanCart® concentrate cartridge dissolves about 32 grams of citric acid into the purified water. It should be appreciated however that citric acid concentrates providing more or less than 32 grams of citric acid are contemplated and within the scope of the present disclosure.

In the example of system 10a, a liquid citric acid concentrate source 86 is used instead of the dry powder concentrate. Here, a jug or container 86 of liquid citric acid concentrate is placed in fluid communication with dialysis fluid circuit 30 and in particular the concentrate and dialysis fluid pumps 38, 44, 54 and 58 of same. The pumps under control of logic implementer 20 may pump all or most all, or alternatively a desired volume, of the liquid citric acid concentrate from the source 86 into the purified water to achieve a mixture having a desired citric acid in purified water concentration, e.g., a diluted citric solution in the range between 0.5% and 10% citric acid, depending on the surface area needing disinfection and decalcification. The 32 grams of citric acid provided by the CleanCart® concentrate cartridge is merely one example.

The process of filling dialysis fluid circuit 30 with water and citric acid may take from about one to about two minutes.

At step 210, logic implementer 20 commands heater 52 to heat the fluid mixture as it is circulated throughout dialysis fluid circuit 30. In one embodiment, logic implementer causes heater 52 to heat the citric acid solution or mixture to a desired temperature, such as 93° C. The inputted temperature will depend upon the altitude at which machine 12 is located because the boiling point of the fluid mixture lowers as the elevation rises. Also, the addition of the physiologically safe cleaning agent, such as citrate, allows the desired temperature to be lowered, e.g., by 10° C. Heater 52 is in one embodiment an inline resistance heater. Heating step 210 may take about five to ten minutes in one embodiment, or even up to twenty minutes depending upon the size of heater 52.

At step 212, logic implementer 20 causes dialysis fluid or dialysis fluid pumps 54 and 58 with bypass valve 92a open to recirculate the heated, fully concentrated citric acid mixture throughout dialysis fluid circuit. Pumps 54 and 58 are operated at a high and perhaps maximum flowrate to obtain a more turbulent flow. The turbulent flow creates friction against the walls of the tubing and components to increase cleaning, including increased mechanical pressure on calcium and magnesium carbonate deposits as well as bacteria, which may try to hide in slots or behind biofilms. The citric acid disinfectant and the heat provide a two-pronged cleaning technique. The circulation and cleaning of step 212 may last from about one (1) to thirty (30) minutes. During recirculation, heat exchanger 66 acts as a heater for the disinfection recirculation circuit 56/78 portion of dialysis fluid circuit 30, which is pumped by used dialysis fluid pump 58. In the other portion of dialysis fluid circuit 30 pumped by fresh dialysis fluid pump 54, heater 52 along with logic implementer 20 and temperature sensor 42 control the temperature at sensor 42 to a desired temperature. In this way, the temperature of the disinfection recirculation circuit 56/78 portion of dialysis fluid circuit that used dialysis fluid pump 58 serves is close to the temperature of the fluid mixture in the portion of dialysis fluid circuit 30 that fresh dialysis fluid pump 54 serves.

At step 214, logic implementer 20 causes used dialysis fluid pump 58, with drain valve 92*d* open, to perform a limited or partial drain. The limited or partial drain may last about one (1) or two (2) minutes and remove about ten percent to seventy-five percent (10% to 75%) of the volume of fluid in dialysis fluid circuit 30 to drain 60. As discussed above, the partial drain creates one or more air slug or pillow within dialysis fluid circuit 30, such that the partial drain removes citric acid from the disinfecting solution or mixture by sending ninety to ninety-five percent (90%-95%) of the citric acid solution to drain 60. The partial drain is therefore almost as effective as a full drain in terms of how much citric acid is flushed. In an embodiment, at the end of the partial or limited drain step 214, approximately all but three (3) grams of the original 32 grams, or approximately 90%, of the citric has been removed from dialysis fluid circuit 30.

At step 216, logic implementer decides if there is another treatment for the day. If another treatment is to be performed as illustrated at step 218, a filling or priming step for the next treatment is performed. Here, logic implementer 20 of system 10*a* or 10*b* closes disinfection recirculation valve 92*c*, opens drain valve 92*d* and purified water valve 92*e*, and runs fresh dialysis fluid pump 54 to pull purified water from source 22 to replace the volume of disinfecting fluid lost via the partial drain at step 214 and to purge systems 10*a* and 10*b* of air. Logic implementer then runs A and B-concentrate pumps 38 and 44 to add A- and B-concentrates from sources 24 and 26, respectively, to form dialysis fluid.

Filling or priming step 218 fills the dialysis fluid circuit 30. When filling dialysis fluid circuit 30 in one embodiment, logic implementer 20 causes purified water from source 22 to flow from the beginning of the machine at source 22 to its end at drain 60. The purified water flow causes remaining pockets of citric acid cleaning solution and air to be flushed to drain 60. A- and B-concentrates are then added to form dialysis fluid. To clean fresh dialysis fluid tube 72, and to prevent recirculation of citric acid from tube 72 into clean water at valve 92*e*, logic implementer 20 may cause used dialysis fluid pump 58 to suck the purified water through bypass line 68, fresh dialysis fluid line 70 and fresh dialysis fluid tube 72.

The first dialysis fluid to reach drain 60 will therefore be blended with a relatively high degree of the citric acid. But dialysis fluid during filling or priming will quickly rid the machine of remaining citric acid solution, e.g., within a liter or less of dialysis fluid flushed to drain 60. In an embodiment, the volume of each filling or priming exchange is about one to three liters, such that at the end of filling or priming step 216, well over 99% of the original amount of citric acid has been removed from system 10. Where an original 32 grams of citric acid is used, less than a gram, e.g., 0.3 gram, of citric acid may remain.

Figure 5:
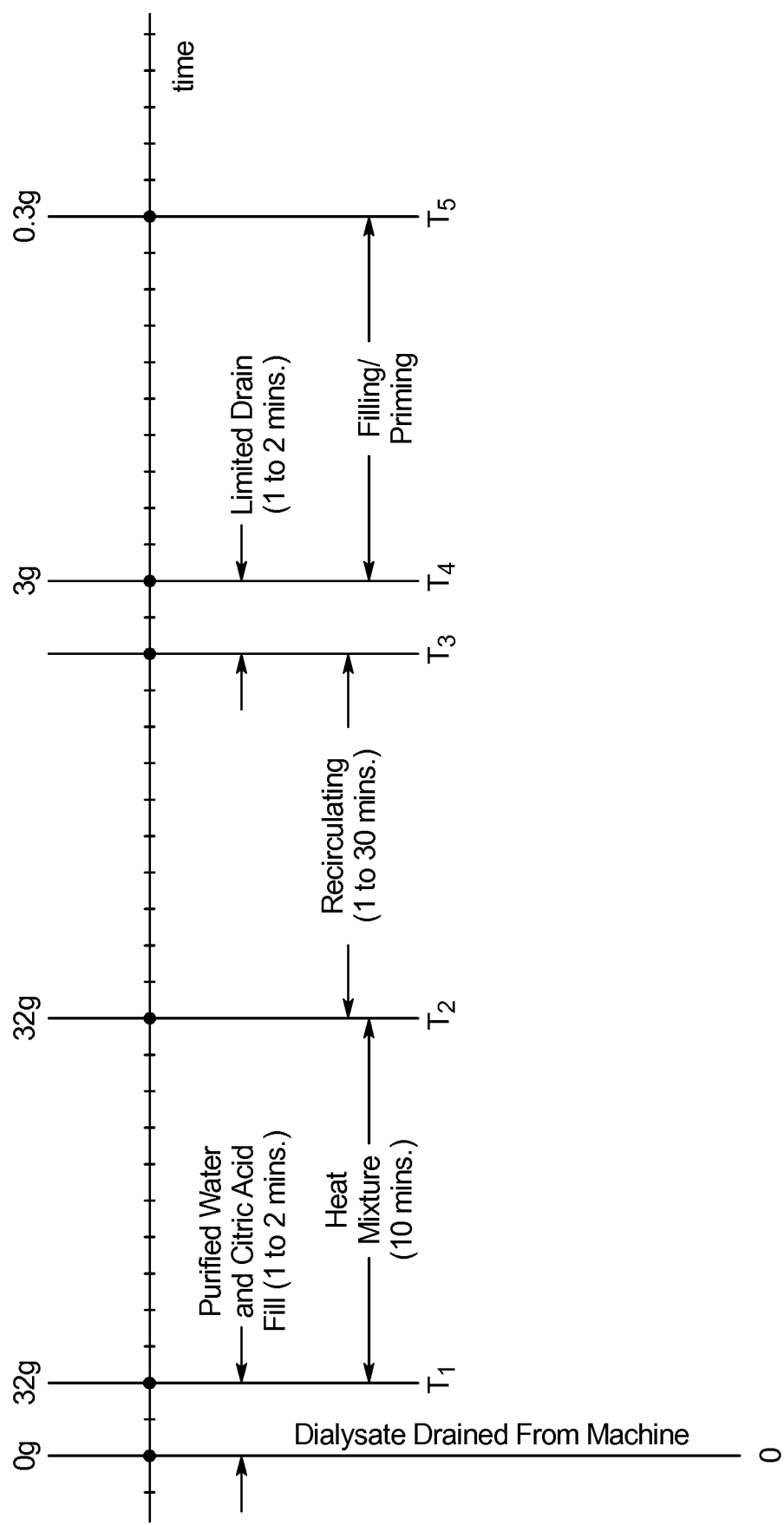
FIG. 5 is an example timeline schematic further illustrating the process flow diagram of FIG. 4.

The timeline of FIG. 5 shows an example where filling or priming step 218 takes the citric acid level from 3 grams to 0.3 grams, removing 2.7 grams. 2.7 grams out of the original 32 grams is about 8.4%. It is contemplated for filling or priming step 218 to remove at least one percent of the original citric acid or other physiological cleaning, disinfecting, and/or decalcifying substance, up to 10% or more depending upon how much physiological cleaning, disinfecting, and/or decalcifying substance remains at the beginning of filling or priming step 218.

At the end of filling or priming step 218, half of the approximately 0.3 gram of citric acid will reside on the fresh dialysis fluid side of dialyzer 102, while the other half of the approximately 0.3 gram of citric acid will reside on the used side of the dialyzer. The 0.15 gram of citric acid residing on the used side will be sent to drain once treatment starts and has no chance of reaching the patient. Of the 0.15 gram of citric acid residing on the fresh dialysis fluid side of dialyzer 102, some may osmose into the blood compartment and be delivered to the patient, but the majority of it will be carried along the outsides of the dialyzer membranes and be flushed to drain 60. Thus the patient will see very little of the original citric acid.

After filling or priming step 218, a second patient performs a second treatment at step 204. Method 200 repeats steps 204 to 218 until no additional treatments remain. At step 216, if no treatments remain, method 200 proceeds to step 220, where at the end of the day, the system 10*a* or 10*b* may be left wet or dry. If wet, logic implementer 20 may fill the dialysis fluid circuit 30 with purified water to compensate for the limited drain. The next day will begin with a filling or priming step to further reduce or eliminate citric acid as described at step 218. If dry, logic implementer 20 may drain dialysis fluid circuit 30 completely, removing all citric acid (which may be done alternatively at step 214 instead of a partial drain if it is known at that time that no further treatments will be performed).

Method 200 ends at step 222.

Importantly, method 200 does not include a rinse cycle after circulation step 212. Instead, method 200 moves directly to a drain cycle in step 214, which may even be a limited drain cycle. Thus, a significant amount of time between treatments is saved. As described herein, the skipping of the rinse cycle is enabled through the use of a physiological cleaning, disinfecting, and/or decalcifying cleaning agent, such a citric acid. In one embodiment, as illustrated in FIGS. 1A and 1B, a connector 94*a* associated with the source 86, 90 of physiological cleaning, disinfecting, and/or decalcifying substance and a mating connector 94*b* associated with machines 12 of systems 10*a* and 10*b* are keyed or configured so that machine 12 may only accept a certain type or brand of cleaning agent, namely, a physiologically safe cleaning, disinfecting, and/or decalcifying substance. Here, if a user tries to plug a different type or brand of cleaning agent, e.g., which is not physiologically safe, into connector 94*b*, connection will be prevented. Such keying and/or configuring of connectors 94*a* and 94*b* ensures that the cleaning agent connected to machine 12 is appropriate for skipping the disinfecting rinse and the running the limited drain.

Moreover, besides the keying or configuring of connectors 94*a* and 94*b*, it is contemplated to package the source 86, 90 of physiological cleaning, disinfecting, and/or decalcifying substance so as to ensure that it is a single use package. For example, the package may have a film that is permanently punctured or a tab that is permanently removed to show that it is to be used once and then discarded. Suitable writings and indicia may also mark the package or source 86, 90 as being single use. In this way, a user is dissuaded from refilling the package with a non-physiological cleaning, disinfecting, and/or decalcifying cleaning agent. Alternatively or additionally to the puncture films, removable tabs and suitable indicia, the packaging for sources 86, 90 may have a one-way valve or flap that physically prevents a user from reloading the source with a non-physiologically safe cleaning agent.

Alternatively, or in addition to the use of mated keyed connectors 94*a* and 94*b* and/or the single use packages or sources 86, 90, physiological cleaning, disinfecting, and/or decalcifying substance may be provided with a marking 85, such as a barcode, 3D barcode, radio frequency identifier ("RFID") chip or any type of indicia that may be read by a corresponding scanner, reader, RFID reader, or camera 15. In the illustrated embodiment, scanner, reader, RFID reader, or camera 15 is provided with user interface 14 of machine 12, and thus communicates with one or more processor 16 and memory 18 of logic implementer 20. Scanner, reader, RFID reader, or camera 15 may be provided at the end of a cord or be flush mounted to machine 12.

One or more processor 16 of logic implementer is programmed during treatment setup to read marking 85 on source 86, 90 at scanner, reader, RFID reader, or camera 15 prior to the connection of the source to machine 12 of system 10a or 10b. That way, machine 12 knows if the cleaning agent is physiologically safe or not. If not, logic implementer 20 is programmed to run a standard treatment sequence, including a fresh water rinse after disinfection and a full drain after the rinse. If scanner, reader or camera 15 reads that the source 86, 90 is physiologically safe, logic implementer determines that machine 12 may instead run the shortened treatment sequence of method 200. Logic implementer 20 may cause user interface 14 to display a suitable audio, visual or audiovisual message asking for confirmation of the shortened sequence, such as, "Clean-Cart® cartridge detected, please [confirm] or [cancel] no rinse and limited drain." The user may then press [confirm] or [cancel] to accept or reject the shorter transition between treatments. In an embodiment, no rinse and limited drain are enabled only when scanner, reader, RFID reader, or camera 15 detects that the source 86, 90 is physiologically safe.

Further additionally or alternatively to the use of mated keyed connectors 94a and 94b, single use packages, and/or markings 85 and scanner, reader, RFID reader, or camera 15, machine 12 (i) just upstream or downstream of valve 92f in FIG. 1A or (ii) just downstream of connector 94b in FIG. 1B may place a pH detector and/or conductivity sensor (not illustrated) for detecting the pH and/or conductivity of the cleaning agent just as it begins to enter dialysis fluid circuit 30. The readings from pH detector and/or conductivity sensor are sent to logic implementer 20. Logic implementer 20 may be programmed to, for example, use the readings to determine that the source 86, 90 is (i) not physiologically safe and run a standard disinfectant rinse and drain, notifying the user of same via user interface 14 or (ii) physiologically safe and run method 200 with no disinfectant rinse and limited drain, notifying the user of same via user interface 14. Alternatively, the readings are used to confirm that source 86, 90 is physiologically safe after being told so by the user or determining so via scanner, reader, RFID reader, or camera 15.

Referring now to FIG. 5, an example timeline summarizing the timing and results of method 200 is illustrated. All values used in connection with FIG. 5 are example values and are not meant to be limiting or necessary. At time zero, treatment has already been performed and the used dialysis fluid has been drained completely from dialysis fluid circuit 30. At time T1 (end of step 208), e.g., at 1 or 2 minutes, dialysis fluid circuit 30 is filled with purified water and citric acid, e.g. 32 grams. At time T2 (end of step 210) the, e.g., 32 grams of citric acid remains and the mixture has been heated over about ten minutes. At time T3 (end of step 212), the disinfecting mixture has been circulated in a cleaning manner for about one (1) to thirty (30) minutes. At time T4 (end of step 214) a limited drain has been performed for about one (1) to two (2) minutes, bringing the citric acid down to, e.g., 3 grams. In an embodiment, at least 85% of the citric acid has been removed by time T4. At time T5 (end of step 218) a system 10 filling sequence with exchanges is performed, flushing virtually all the remaining citric acid, e.g., bringing the citric acid level down to 0.3 gram or below.

In another example, if at time T4 (at the end of limited drain), the citric acid level is only 0.5 gram, the filling sequence with exchanges may bring the citric acid level down to 0.18 gram. Here, 0.32 gram or one percent of the original 32 grams of citric acid or physiological cleaning, disinfecting, and/or decalcifying substance is removed. As discussed above, it is contemplated to remove at least one percent of the original citric acid or other physiological cleaning, disinfecting, and/or decalcifying substance.

The total time range from time T0 to time T4 is from thirteen minutes (1+10+1+1) to forty-four minutes (2+10+30+2).

As discussed above, patients using citrate anticoagulant tolerate six (6) to twelve (12) grams of citrate per hour. Method 200 removes citric acid to a much lower level. Thus some steps of method 200 may be reduced or eliminated. For example, cleaning or circulating step 212 may be shortened or eliminated if enough citric acid may be removed in steps 214 and 216. Or, the limited drain step 214 may be shortened or eliminated if enough citric acid may be removed in steps 212 and 216. Or, the priming exchanges may be shortened or eliminated if enough citric acid may be removed in steps 212 and 214. Any of the alternatives listed may be combined with a varying amount of initially supplied citric acid, e.g., from twenty (20) to fifty (50) grams, to achieve a desired amount of disinfection.

The present disclosure is also not limited to citric acid and applies to other physiological cleaning, disinfecting, and/or decalcifying substance, which may be added from a source to purified water from its source 22 to form a mixture, and which may be circulated within the dialysis fluid circuit using the dialysis fluid pump to disinfect and/or clean and/or decalcify the dialysis fluid circuit after a first treatment, and where the this disinfection procedure does not require a subsequent rinse procedure. The physiological cleaning, disinfecting, and/or decalcifying substance may be an acid, such as citric acid, lactic acid, malic acid, acetic acid, and gluconic acid, or any combination thereof. The substance may also be an acid, such as any one or more above, in combination with another physiologically safe substance, such as salts and/or sugars.

Note, in order to be able to cool the dialysis machine of system 10, logic implementer 20 may alternatively regulate the dialysis fluid temperature to some temperature lower than the normally required 35° C. to 38° C., for example, to 25° C. to 30° C. to cool the machine with start-up solution or priming solution during filling or online priming.

Figure 6:
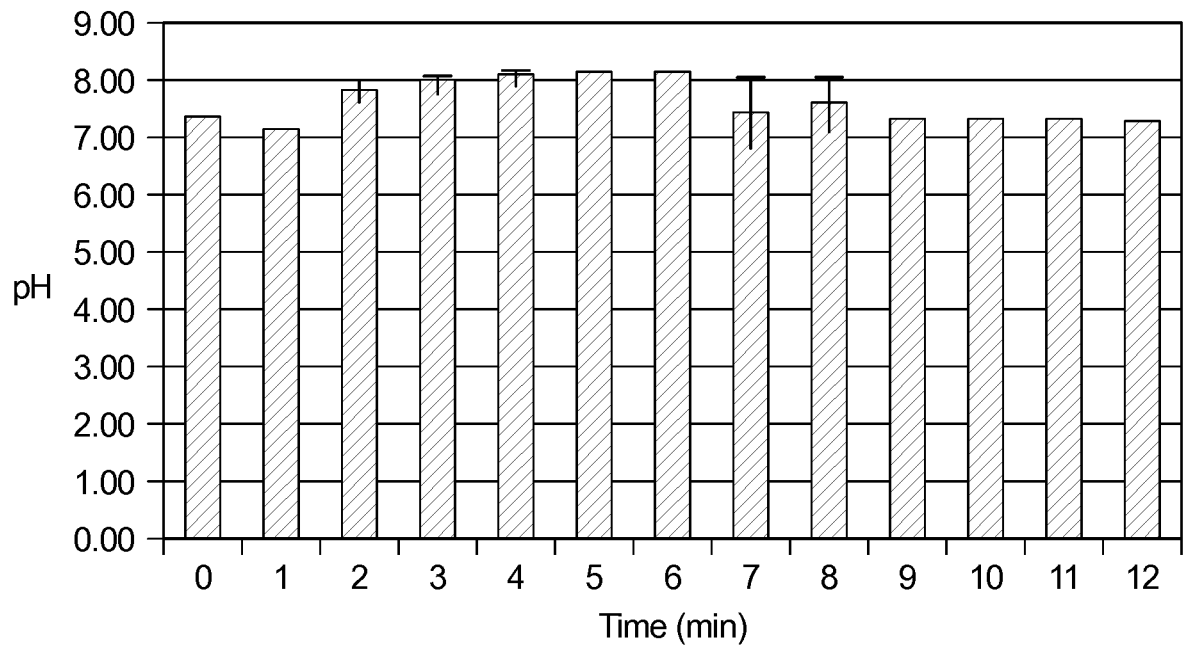
FIG. 6 is a chart illustrating one example of pH balancing or recovery during priming using bicarbonate concentrate with residual citric acid and purified water.
Figure 7:
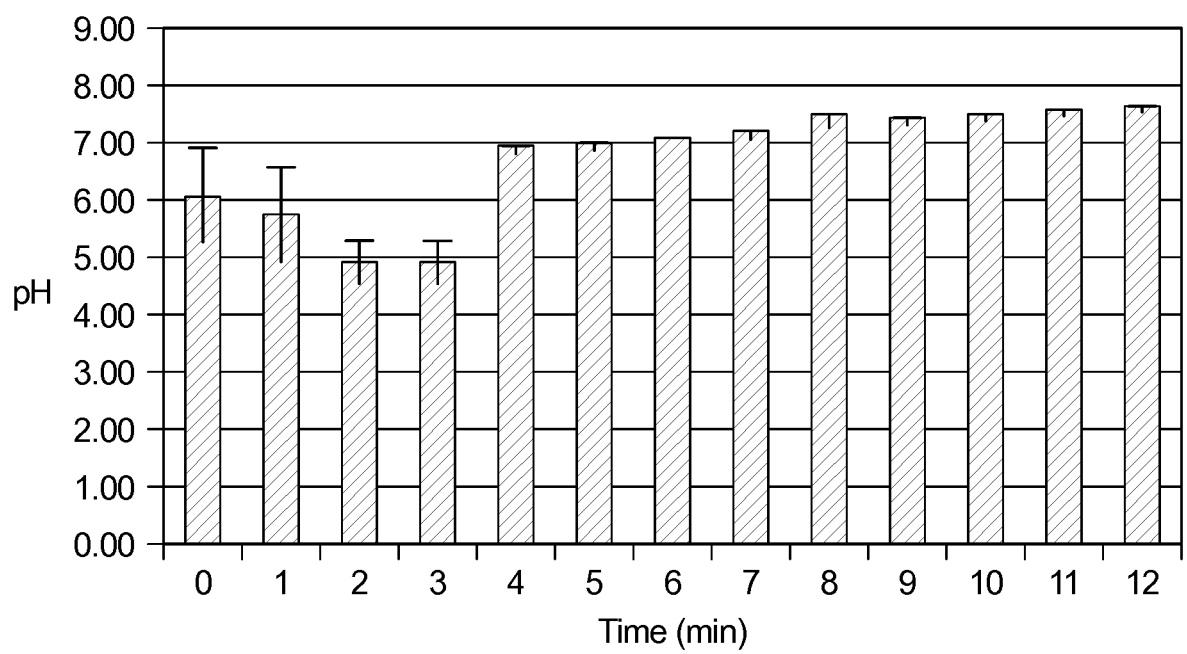
FIG. 7 is a chart illustrating one example of pH balancing or recovery during priming using acetate concentrate with residual citric acid and purified water.

Referring now to FIGS. 6 and 7, graphs illustrating that residual citric acid at the beginning of filling or priming will not negatively impact the creation of dialysis fluid are illustrated. In particular, FIGS. 6 and 7 show the impact of the residual citric acid on the pH of the newly formed dialysis fluid. FIG. 6 illustrates pH recovery for a bicarbonate treatment (much more common), while FIG. 7 illustrates pH recovery for an acetate treatment. For bicarbonate treatment in FIG. 6, the dialysis fluid never becomes acidic and indeed it takes nine minutes for the pH to drop to neutral to reach a "green fluid path", meaning treatment may proceed. As mentioned above, citrate and citric acid are not exactly the same. But when citric acid meats bicarbonate, the citric acid reacts and becomes citrate, leaving an initial dip in bicarbonate. For acetate treatment in FIG. 7, the dialysis fluid becomes acidic for the first four minutes but reaches the "green fluid path" (treatment may proceed) at around six minutes. In both cases, "green fluid path", or ready for delivery is reached in a reasonable time period. Also, in both cases the ready to be delivered point or stage is reached after a time when citric acid impact is still measurable.

It should be understood that various changes and modifications to the presently preferred embodiments described herein will be apparent to those skilled in the art. Such changes and modifications may be made without departing from the spirit and scope of the present invention and without diminishing its intended advantages. It is therefore intended that such changes and modifications be covered by the appended claims.

The invention is claimed as follows:

1. A renal failure therapy system comprising:
a dialysis fluid circuit including a dialysis fluid pump;
a source of physiological cleaning, disinfecting, and/or decalcifying substance in fluid communication with the dialysis fluid circuit;
a source of purified water in fluid communication with the dialysis fluid circuit; and
a logic implementer in operable communication with the dialysis fluid pump, wherein the logic implementer is programmed such that the system is configured to:
cause the physiological cleaning, disinfecting, and/or decalcifying substance to be added from its source to purified water from the purified water source to form a mixture,
circulate the mixture within the dialysis fluid circuit using the dialysis fluid pump to at least one of clean, disinfect, or decalcify at least a portion of the dialysis fluid circuit without a subsequent rinse after circulating and moving directly to a drain sequence,
cause a portion of the mixture to be drained in the drain sequence, wherein draining a portion of the mixture from the dialysis fluid circuit includes trapping air in the dialysis fluid circuit, and
cause a filling procedure for a second treatment to begin with a portion of the mixture remaining in the dialysis fluid circuit, wherein the filling procedure reduces the remaining mixture to a lower level and removes a portion of the remaining mixture to drain.

2. The renal failure therapy system of claim 1, wherein the physiological cleaning, disinfecting, and/or decalcifying substance includes an acid.

3. The renal failure therapy system of claim 2, wherein the acid is at least partially citric acid.

4. The renal failure therapy system of claim 1, wherein the physiological cleaning, disinfecting, and/or decalcifying substance includes citric acid in combination with a physiologically safe substance.

5. The renal failure therapy system of claim 1, wherein the threshold amount is one percent of an amount of physiological cleaning, disinfecting, and/or decalcifying substance added from its source to purified water to form the mixture.

6. The renal failure therapy system of claim 1, wherein the filling procedure involves an introduction of a bicarbonate substance from a source that neutralizes the physiological cleaning, disinfecting, and/or decalcifying substance.

7. The renal failure therapy system of claim 1, wherein the filling procedure removes at least one percent of an original amount of the physiological cleaning, disinfecting, and/or decalcifying substance.

8. The renal failure therapy system of claim 1, which includes a heater, the logic implementer programmed to control the heater such that a filling fluid is introduced to the dialysis fluid circuit during the filling procedure at a temperature below 35° C.

9. The renal failure therapy system of claim 8, wherein the logic implementer is further programmed to cause the heater to heat the mixture while at least one of cleaning, disinfecting, or decalcifying the at least a portion of the dialysis fluid circuit.

10. The renal failure therapy system according to claim 1, which includes at least one of (i) a keyed connector for the source of physiological cleaning, disinfecting, and/or decalcifying substance and a mating keyed connector for dialysis fluid circuit, or (ii) a marking associated with the source of physiological cleaning, disinfecting, and/or decalcifying substance and a scanner, reader, RFID reader, or camera in communication with logic implementer for reading the marking, upon which the logic implementer can allow or confirm the circulating of the mixture without the subsequent rinse.

11. The renal failure therapy system according claim 1, wherein the dialysis fluid circuit includes a disinfection recirculation loop and an air separation chamber located within the loop, the air separation chamber increasing at least one of a flowrate and a heating efficiency of the physiological cleaning, disinfecting, and/or decalcifying substance flowing within the disinfection recirculation loop.

12. The renal failure therapy system according claim 1, wherein the logic implementer is further programmed to:
cause purified water to flow from the source of purified water to a drain, the purified water flow causes remaining pockets of the physiological cleaning, disinfecting, and/or decalcifying substance and air to be flushed to drain; and
add a concentrate to the purified water to form dialysis fluid,
wherein forming the dialysis fluid causes the at least a portion of the remaining part of the mixture to be removed to drain.

13. A renal failure therapy machine operable with a source of physiological cleaning, disinfecting, and/or decalcifying substance and a source of purified water, the machine comprising:
a dialysis fluid circuit including a dialysis fluid pump, the dialysis fluid circuit configured to pump from the physiological cleaning, disinfecting, and/or decalcifying substance source and the purified water source; and
a logic implementer in operable communication with the dialysis fluid pump, the logic implementer programmed such that the machine is configured to cause:
the physiological cleaning, disinfecting, and/or decalcifying substance from its source to be added to purified water from the purified water source to form a mixture and to circulate the mixture within the dialysis fluid circuit using the dialysis fluid pump to at least one of clean, disinfect or decalcify at least a portion of the dialysis fluid circuit after a first treatment,
a portion of the mixture to be drained in a drain sequence that begins directly after circulation of the mixture and without a separate rinsing sequence in between, wherein the drain sequence includes trapping air in the dialysis fluid circuit while draining the portion of the mixture, and
a filling procedure for a second treatment to begin directly after the drain sequence, and without a separate rinsing sequence in between, with the mixture remaining in the dialysis fluid circuit, the filling procedure relied upon to reduce the mixture remaining to a lower level.

14. The renal failure therapy machine of claim 13, wherein the logic implementer is programmed to circulate the mixture within the dialysis fluid circuit from about one to about thirty minutes.

15. The renal failure therapy machine of claim 13, wherein, during the filling procedure, at least one percent of an original amount of the physiological cleaning, disinfecting, and/or decalcifying substance is removed.

16. The renal failure therapy machine according to claim 13, wherein, during the filling procedure, a bicarbonate substance from a source is provided, which neutralizes the physiological cleaning, disinfecting, and/or decalcifying substance.

17. The renal failure therapy machine according to claim 13, wherein the drained portion of the mixture is a first portion, and wherein the logic implementer is further programmed to move to the second treatment including performing a filling procedure that drains a second portion of the mixture.

\* \* \* \* \*